United States Patent [19]
Downs

[11] Patent Number: 4,481,294
[45] Date of Patent: Nov. 6, 1984

[54] PROCESS FOR CELL DISRUPTION

[75] Inventor: John D. Downs, Sittingbourne, England

[73] Assignee: Shell Oil Company, Houston, Tex.

[21] Appl. No.: 435,438

[22] Filed: Oct. 20, 1982

[30] Foreign Application Priority Data

Nov. 3, 1981 [GB] United Kingdom ................ 8133059

[51] Int. Cl.³ ...................... C12N 1/06; C07G 17/00; C13L 3/00; C12R 1/38
[52] U.S. Cl. ................................... 435/259; 435/267; 435/274; 435/874; 435/101; 435/104
[58] Field of Search ............... 435/101, 104, 240, 259, 435/261, 262, 267, 274, 874, 281; 252/8.55 D; 166/246

[56] References Cited

U.S. PATENT DOCUMENTS 3,598,181 8/1971 Wegner et al. ..................... 166/246
3,966,618 6/1976 Colegrove ........................... 435/104
4,165,257 8/1979 Stokke ................................. 435/262

OTHER PUBLICATIONS

Birnboim et al., Nuclei Acids Res. vol. 7, #6, 1979, pp. 1513-1523.
"Methods in Microbiology", Ed. Norris and Ribbons, Publ. Academic Press, London and New Yori, 5B, pp. 371-372 (1971).

Primary Examiner—Raymond Jones
Assistant Examiner—Marianne S. Minnick

[57] ABSTRACT

Process for disrupting cells by contacting an aqueous, cell-containing medium with a protease enzyme, wherein the enzymic contact is preceded by contact with an ionic surfactant; the polysaccharide solutions thereby produced; and a process for displacing a fluid through a well and/or a permeable subsurface formation communicating with the well, by injecting into the well an optionally diluted, aqueous solution of such a polysaccharide.

8 Claims, No Drawings

PROCESS FOR CELL DISRUPTION

BACKGROUND OF THE INVENTION

1. Field of the Invention

This invention relates to an improved method for disrupting cells, and in particular to a process for disrupting the cells in a broth obtained by fermentation of a nutrient medium with a polysaccharide-producing microorganism.

2. Description of the Prior Art

In microbiological processes it is often necessary in the later stages to disrupt the bacterial cells. This requirement occurs, for example, in the preparation of intracellular enzymes, when the cell must be broken open to release the enzyme. Another example in a quite different technological context arises in the microbial production of polysaccharides for use as viscosifiers in enhanced oil recovery. In this application the hydrophilic polysaccharides or xanthan gums are added at a low concentration to water flooding operations to increase the viscosity of the aqueous system and thereby bring about more efficient, piston-type, displacement of the oil from the reservoir rock. These microbial polysaccharides appear to be particularly well suited for this polymer flooding application in that they exhibit in aqueous systems a high viscosity at low concentration that is stable to the high shear rates encountered at the point of injection into the oil-bearing formation and which is largely insensitive to high salt concentration found in formation waters.

While the outlook for the use of microbial polysaccharides in enhanced oil recovery would appear to be promising, certain problems have been encountered in practice, including the insoluble impurities present in industrial grades of these polysaccharides. In the typical commercial production of polysaccharides by Xanthomonas fermentation, the high viscosity of the fermentation broth precludes complete separation of insoluble material, such as cellular debris and nonviable bacteria, from the polysaccharide-containing broth. As a result, commercial grades of these microbial polysaccharides may contain solids which do not dissolve in dilute aqueous solution, such as that required for polymer flooding in enhanced oil recovery. The presence of these particulate solids in the polysaccharide solution presents considerable difficulty in field application of the polymer flood, because they can cause plugging of the rock face and injection water filters. Previous attempts to overcome this plugging problem have included caustic treatment of the polysaccharide solution and subsequent flocculation of the solids, and enzyme treatment to bring about disruption and consequential solubilisation of the bacterial solids in the polysaccharide solution prior to use. In many instances the enzyme treatment is preferred, since the physical/chemical conditions involved are such as to minimize any adverse changes in the desired polysaccharide. However, some microorganisms are resistant to disruption by enzymes, and the present invention is based on the discovery that such microorganisms can be rendered susceptible to enzymic disruption by prior treatment with certain surfactants. The use of surfactants for cell disintegration is known, but the Applicants have unexpectedly discovered that microorganisms which are resistant to attack by either surfactant or enzymes alone can be disrupted by successive treatments with anionic or non-ionic surfactant and protease enzyme.

SUMMARY OF THE INVENTION

Accordingly, the present invention provides a process for disrupting cells by contacting an aqueous, cell-containing medium with a protease enzyme, characterised in that the enzymic contact is preceded by contact with an anionic or non-ionic surfactant. As explained above, and as will be apparent to those skilled in the art, this cell disruption process can be applied in a wide variety of practical situations where it is necessary to disrupt cellular structure, for example to release intracellular enzymes, but the process is of particular value in the degradation/solubilisation of the cellular components in the broth obtained by fermentation of a nutrient medium with a polysaccharide-producing microorganism. In some instances, such microorganisms can be adequately degraded using an enzyme treatment alone, but many other organisms, in particular gram-negative bacteria, have a cell wall more resistant to attack and in these cases the process of the present invention can be particularly advantageous. Thus, slime forming species of Pseudomonas, and especially Pseudomonas sp. NCIB 11592, are known to produce a polysaccharide which has suitable properties for use in enhanced oil recovery, but these organisms are not readily degraded by enzymic treatment alone. However, the sequential treatment by surfactant and then by a protease according to the present invention enables such Pseudomonas cells to be disrupted and thereby solubilised. This makes it possible to produce a polysaccharide solution suitable for use in enhanced oil recovery by (a) cultivation of a suitable Pseudomonas in a nutrient medium; (b) contacting the resultant fermentation broth firstly with an anionic or non-ionic surfactant and subsequently with a protease to degrade the bacterial cells; and (c) filtering the solution to remove any residual solid matter which could block the oil-bearing reservoir rock. As is well known from the literature, protease enzymes may be alkaline, neutral or acid in character. Non-limiting examples are "Alcalase", "Esperase", "Maxazyme", "Maxatase", and "Kitalase". Good results are obtained with Alcalase. If desired, the resulting cell-free polysaccharide solution can then be concentrated for convenient transport, for example by conventional ultrafiltration techniques.

The surfactant may be non-ionic or anionic, but is preferably an anionic surfactant. A wide variety of anionic surfactants are commercially available, and good results have been obtained with alkali metal alkyl sulphates, alkylbenzene sulphonates, sulphated alkanol ethoxylates and sulphated alkanols, especially those in which the alkyl chain contains at least 8 carbon atoms, and in particular an alkali metal, suitably sodium, salt of dodecyl sulphate or of a sulphated alkanol ethoxylate, such as the products marketed as "Dobanol" detergent alkylates. For most effective results the cell-containing medium should be contacted with the surfactant at a pH below about 6.0, preferably below about pH 4.5, whilst the subsequent contact with the enzyme should be at that pH at which the enzyme is most active; for alkaline proteases this pH is above about 6.0, suitably between about pH 7.0 and about pH 9.0. For both the surfactant and the enzyme treatment the temperature is suitably above room temperature but not high enough to degrade the enzyme or the polysaccharide, eg., about 50°–60° C.

As explained earlier, the prime objective in applying the cell disruption process to polysaccharide broths destined for use in enhanced oil recovery is to prevent the cellular debris from causing plugging of the oil-bearing rock. Suitable filtration tests known per se may be carried out to assess the potential extent of this hazard for a particular batch of treated broth, and it has been found that the disruption treatment of this invention achieves substantial improvements in filtration rates through microporous membranes, which are indicative of a significant reduction in any tendency to plugging.

The invention is illustrated in the following Examples:

EXAMPLE I (A) Pseudomonas NCIB 11592 was cultivated under batch conditions in a Chemap LF.7 fermenter containing 4 liters of a mineral salts growth medium shown in Table 1 below. The culture temperature was maintained at 28° C. and the pH controlled at 7.0 by automatic addition of 2M alkali solution (1M NaOH+1M KOH). Air was sparged into the fermenter at 0.5 l min$^{-1}$ and the culture was agitated by 3×4 bladed Rushton turbine impeller revolving at 1000 rpm.

TABLE 1

| Component | Salts Medium | | |
|---|---|---|---|
| | g l$^{-1}$ | mM | μm |
| Glucose | 20.0 | | |
| Na$_2$HPO$_4$ | | 21.13 | |
| KH$_2$PO$_4$ | | 22.04 | |
| (NH$_4$)$_2$SO$_4$ | | 2.27 | |
| MgSO$_4$.7H$_2$O | | 0.81 | |
| CaCl$_2$.2H$_2$O | | 0.10 | |
| FeCl$_3$.6H$_2$O | | | 244.6 |
| MnSO$_4$.4H$_2$O | | | 1.34 |
| ZnSO$_4$.7H$_2$O | | | 1.25 |
| CuSO$_4$.5H$_2$O | | | 1.28 |
| CoCl$_2$.6H$_2$O | | | 1.51 |
| H$_3$BO$_3$ | | | 2.23 |
| Na$_2$MoO$_4$.2H$_2$O | | | 2.47 |
| Casamino acids | 1.0 | | |

Approximately 120 hours after inoculation the residual glucose in the fermentation broth had been exhausted by microbial metabolism and the culture was harvested and stored at 5° C. until required for enzyme treatment. The final concentration of cells and polysaccharide in the broth were 1.34 gl$^{-1}$ and 9.1 gl$^{-1}$ respectively, as adjudged by dry weight determination. The viscosity of the broth after nine-fold dilution with distilled water was found to be 27 centipoise at a shear rate of 23 sec$^{-1}$ as measured in a Brookfield LVT viscometer.

(B) A sample of fermentation broth (100 ml) was titrated to pH 4.0 with 2M sulphuric acid and the detergent, sodium dodecyl sulphate, added to a final concentration of 1 gl$^{-1}$. The sample was incubated in a 250 ml conical flash on an orbital shaker at 60° C. for approximately 1 hour. The culture was then re-titrated to pH 9.0 with 2M sodium hydroxide and a bacterial alkaline protease in liquid concentrate form, Alcalase 0.6 L (Novo Enzyme Products Ltd., Windsor, England), was added to a final concentration equivalent to 1 Anson unit protease activity/g. bacterial cell protein. The sample was then incubated for a further 20 hours at 60° C. on an orbital shaker, during which time the proteolytic digestion of the cells visibly clarified the fermentation broth. The optical density of the culture measured at 600 nm on a Cecil CS 595 spectrophotometer decreased from 3.30 to a minimum value of 0.60 within 4 hours of the enzyme addition. This was associated with a decrease in culture cell dry weight concentration from 1.34 gl$^{-1}$ down to 0.56 gl$^{-1}$. Microscopic examination of the clarified broth revealed that complete disintegration of the bacterial cell bodies had taken place, leaving a residue of cell wall fragments <0.1μ in diameter.

(C) Filtration tests were carried out on the clarified broth diluted nine-fold with distilled water to give a 1000 ppm polysaccharide solution containing 62 ppm insoluble solids, either as undigested cell wall material or insoluble salt precipitate. The diluted solution was filtered through 47 mm diameter Millipore filter pads of 0.65μ and 0.45μ pore diameter, using an over pressure of 15 psi. The cumulative weight of filtrate collected versus time was noted. Tables 2 and 3 show typical filtration rates through 0.65μ and 0.45μ pore filters respectively. In both cases the clarified broth filtration rates were considerably faster than the filtration rates obtained using similarly diluted samples of unclarified broth.

TABLE 2

Filtration of diluted Ps. NCIB 11592 fermentation broth through Millipore filters, 0.65μ pore diameter

| Cumulative | Cumulative time (seconds) | |
|---|---|---|
| Volume (ml) | Untreated broth | SDS/Alcalase treated |
| 10 | 3.0 | — |
| 25 | 18.5 | 3.6 |
| 50 | 720.0 | 9.1 |
| 100 | — | 23.9 |
| 150 | — | 47.7 |
| 200 | — | 83.8 |
| 250 | — | 138.1 |

TABLE 3

Filtration of diluted Ps. NCIB 11592 fermentation broth through Millipore filters, 0.45μ pore diameter

| Cumulative | Cumulative time (seconds) | |
|---|---|---|
| Volume (ml) | Untreated broth | SDA/Alcalase treated |
| 5 | 10.0 | — |
| 10 | 39.0 | 4.0 |
| 15 | 115.0 | 7.5 |
| 20 | 505.0 | 15.4 |
| 25 | — | 40.5 |
| 30 | — | 175.6 |

EXAMPLE II

Further experiments were carried out to determine the extent to which the effectiveness of process is influenced by the pH of the treatment and the concentration of the detergent and enzyme. These experiments were carried out using a fermentation broth of Pseudomonas sp. NCIB 11592 prepared by a similar procedure to that described in Example IA, but using the following medium:

| Component | Concentration |
|---|---|
| Glucose | 30 g/l |
| Citric acid | 100 μM (as chelating agent) |
| KH$_2$PO$_4$ | 5 mM |
| NH$_4$Cl | 16 mM |
| MgSO$_4$7H$_2$O | 1 mM |
| FeSO$_4$7H$_2$O | 100 μM |
| CaCl$_2$2H$_2$O | 100 μM |
| ZnSO$_4$7H$_2$O | 5 μM |
| MnSO$_4$4H$_2$O | 5 μM |

-continued

| Component | Concentration |
|---|---|
| $CuSO_4 5H_2O$ | 1 μM |
| $CaCl_2 6H_2O$ | 1 μM |

The pH was controlled at pH 7 with 2M alkali solution. The broth was harvested about 90 hours after inoculation and the individual treatments were then carried out with a 30 ml sample of broth which was incubated at 50° C. with sodium dodecyl sulphate (SDS) and/or Alcalase in a 250 ml flask on an orbital shaker. The incubation time was 40 minutes for SDS treatment, but for the enzyme treatment was varied as shown in Table 4. The degree of clarification was then determined by diluting the treated broth with 19 volumes of distilled water and measurement of optical density in a Pye Unicam SP6-500 at 625 nm, 10 mm path length, with distilled water as the blank. The optical density of untreated broth at the same dilution was 0.140, which corresponds to a cell dry weight in the undiluted broth of about 1.3 g/l. The results of these tests are set out in Table 4 below.

TABLE 4

| 1st pH | SDS g/l | 2nd pH | Alcalase ml/l | incubation time hrs. | O.D |
|---|---|---|---|---|---|
| 7 | 0 | 7 | 0.17 | 16 | 0.140 |
| 7 | 1 | 7 | 0.17 | 16 | 0.075 |
| 7 | 3 | 7 | 0.17 | 16 | 0.034 |
| 7 | 0 | 7 | 0.33 | 16 | 0.136 |
| 7 | 1 | 7 | 0.33 | 16 | 0.123 |
| 7 | 3 | 7 | 0.33 | 16 | 0.030 |
| 4 | 0 | 7 | 0.33 | 16 | 0.152 |
| 4 | 1 | 7 | 0.33 | 16 | 0.025 |
| 4 | 0 | 8 | 0.67 | 13 | 0.128 |
| 4 | 0.2 | 8 | 0.67 | 13 | 0.059 |
| 4 | 1.0 | 8 | 0.67 | 13 | 0.027 |
| 4 | 1.5 | 8 | 0.67 | 13 | 0.026 |
| 4 | 1.0 | 8 | 0.17 | 13 | 0.033 |
| 4 | 1.0 | 8 | 0.33 | 13 | 0.031 |
| 4 | 1.0 | 8 | 0.67 | 13 | 0.027 |
| 4 | 1.0 | 8 | 1.33 | 13 | 0.023 |
| 2.7 | 1.0 | 8 | 0.67 | 13 | 0.027 |
| 4.0 | 1.0 | 8 | 0.67 | 13 | 0.027 |
| 4.8 | 1.0 | 8 | 0.67 | 13 | 0.032 |
| 4 | 1.0 | 6 | 0.67 | 13 | 0.028 |
| 4 | 1.0 | 7 | 0.67 | 13 | 0.030 |
| 4 | 1.0 | 8 | 0.67 | 13 | 0.028 |
| 4.3 | 1 | 8 | 0 | 3 | 0.105 |
| 4.3 | 1 | 8 | 0.67 | 3 | 0.034 |
| 4.3 | 1 | 8 | 1.33 | 3 | 0.029 |
| 4.3 | 1 | 8 | 2.67 | 3 | 0.028 |
| 4.3 | 1 | 8 | 6.67 | 3 | 0.026 |
| 4.3 | 1 | 8 | 6.67 | 1½ | 0.030 |

EXAMPLE III

Following procedures similar to those described in Example II, a fermentation broth was prepared from Pseudomonas sp. NCIB 11592, and samples were treated with different detergents followed by Alcalase enzyme. The detergents used were:

Anionic: Sodium dodecyl sulphate (SDS).
"Dobanol" 25-3S, sodium salt, a sulphated alkanol ethoxylate.
"Dobanol" 23-2S, sodium salt, a sulphated alkanol ethoxylate.
"Teepol" HB6, sodium salt of $C_{9-13}$ primary alcohol sulphate.
"Dobanic" acid 83, an alkylbenzene sulphonate.
"Dobanic" acid JN, an alkylbenzene sulphonate.
Non-ionic "Triton" X-100, an octylphenol ethyleneoxide condensate.
Cationic: Cetyltrimethyl ammonium bromide.
Dodecylbenzyl dimethyl ammonium chloride.

Both detergent and enzyme incubations were carried out at 50° C., the former for 40 minutes and the latter for 120 minutes. Apart from the "Dobanic" acid detergents, the pH after detergent incubation is little different from that before detergent addition.

The two cationic surfactants caused a rapid and total precipitation of polymer and cells; the results obtained with the anionic and non-ionic detergents are set out in Table 5 below.

TABLE 5

| sample No. | pH before detergent addition | detergent g/l | pH after detergent incubation | Alcalase ml/l | O.D. | final pH |
|---|---|---|---|---|---|---|
| SDS | | | | | | |
| 1 | 4.0 | 0 | | 0 | 0.127 | 6.6 |
| 2 | 4.0 | 0 | | 1.0 | 0.122 | 6.2 |
| 3 | 4.0 | 1.0 | | 1.0 | 0.026 | 6.5 |
| Dobanol 25-3S-27, Na⁺salt | | | | | | |
| 4 | 4.0 | 1.0 | | 1.0 | 0.031 | 7.2 |
| 5 | 4.6 | 1.0 | | 1.0 | 0.033 | 7.3 |
| Dobanol 23-2S-70 Na⁺salt | | | | | | |
| 6 | 4.0 | 1.0 | | 1.0 | 0.027 | 7.7 |
| 7 | 4.6 | 1.0 | | 1.0 | 0.029 | 7.7 |
| Teepol HB6 | | | | | | |
| 8 | 3.3 | 1.0 | | 1.0 | 0.034 | 7.0 |
| 9 | 4.0 | 1.0 | | 1.0 | 0.034 | 8.1 |
| 10 | 4.6 | 1.0 | | 1.0 | 0.037 | 8.0 |
| Dobanic Acid 83 | | | | | | |
| 11 | 4.6 | 1.0 | 4.2 | 1.0 | 0.026 | 8.4 |
| 12 | 5.2 | 1.0 | 4.8 | 1.0 | 0.027 | 8.6 |
| 13 | 6.8 | 1.0 | 6.2 | 1.0 | 0.042 | 8.5 |
| Dobanic Acid JN/X | | | | | | |
| 14 | 4.6 | 1.0 | 4.2 | 1.0 | 0.026 | 8.8 |
| 15 | 5.2 | 1.0 | 4.7 | 1.0 | 0.028 | 8.9 |
| 16 | 6.8 | 1.0 | 6.3 | 1.0 | 0.042 | 8.6 |
| Triton X 100 | | | | | | |
| 17 | 4.0 | 1.0 | | 1.0 | 0.058 | 7.3 |

COMPARATIVE EXAMPLE A

Use of Enzyme Alone

A broth was prepared by fermentation of Pseudomonas NCIB 11592 as described in Example IA above.

Bench-scale surfactant/enzyme treatment of the fermentation broth was carried out using 100 ml samples of broth in 250 ml conical flasks, agitated on a controlled temperature orbital shaker. Examples of the various standard proteolytic enzyme treatments, lysozyme treatments and surfactant treatments are shown in Table 6 together with brief details of conditions used. The effectiveness of each treatment was evaluated by means of optical density measurements at 600 nm, measurement of insoluble cell material remaining in the broth by dry weight determination and microscopic examination. Details of the enzymes evaluated, the conditions applied, and their (in)effectiveness in achieving cell lysis, are given in Table 5, from which it will be seen that proteolytic enzyme treatment alone, either on whole fermentation broth or on Ps. NCIB 11592 cells suspended in phosphate buffer was ineffective. Likewise, lysozyme treatment with or without the use of EDTA and Tris buffer, was not sufficient to lyse Ps. NCIB 11592 cells subjected to osmotic shock.

TABLE 6

| Treatment | Enzyme Origin | Enzyme type/ Trade name | Conditions pH | Temperature (°C.) | Cell Lysis |
|---|---|---|---|---|---|
| Protease (Alkaline) | Bacterial | Alcalase | 7–12 | 40–60 | No |
| Protease (Alkaline) | Bacterial | Esperase | 7–12 | 40–60 | No |
| Protease (Alkaline) | Bacterial | Savinase | 7–12 | 40–60 | No |
| Protease (Neutral) | Bacterial | Neutrase | 5–8 | 20–60 | No |
| Protease (Neutral) | Animal pancreas | Trypsin Chymotrypsin | 6–7 | 20–30 | No |
| Lysozyme | Egg White | Lysozyme | 7–8 | 25 | No |
| Lysozyme + EDTA + Tris | Egg White | Lysozyme | 7–8 | 25 | No |

COMPARATIVE EXAMPLE B

Use of Detergent Alone

A fermentation broth was prepared and treated as in Example II, except that the enzyme was omitted—i.e. after the SDS treatment the pH of the broth was adjusted (if necessary) to pH7 and the broth incubated for 16 hours at 50° C. but in the absence of enzyme. The effectiveness of each treatment is assessed by measurement of optical density (of a sample diluted ×20 with distilled water at 625 nm, 10 mm path length, against distilled water blank). The results are set out in Table 7 below, and by comparison with Table 4 it is apparent that the reduction in optical density (i.e. clarification) is considerably less than is obtained when both SDS and enzyme are used.

TABLE 7

| Initial pH | 7 | 7 | 7 | 7 | 4 | 4 | 4 |
|---|---|---|---|---|---|---|---|
| SDS concn. g/l | 0 | 1 | 3 | 6 | 0 | 1 | 3 |
| O.D. | 0.145 | 0.159 | 0.095 | 0.095 | 0.146 | 0.121 | 0.080 |

COMPARATIVE EXAMPLE C

Use of Detergent After Enzyme Treatment ("Inverse" Treatment)

A fermentation broth was prepared and treated as in Example II, except that the SDS treatment followed—instead of preceded—the enzyme treatment. In order to make the results as closely comparable as possible with those of the invention, the enzyme treatment was preceded by incubation at pH 7 or 4 and 50° C. for 40 minutes (i.e. the conditions used for the SDS treatment), and the broth was then incubated in the presence of SDS at 50° C. for 50 minutes. The extent of clarification was assessed by optical density and the results obtained are set out in Table 8 below, from which it is apparent that the application of the detergent and enzyme treatments in inverse sequence results in a virtually total loss of the ability to clarify the broth.

TABLE 8

| 1st pH | 2nd pH | Alcalase ml/l | 3rd pH | SDS g/l | O.D |
|---|---|---|---|---|---|
| 7 | 6.5 | 0 | 3.6 | 0 | 0.146 |
| 7 | 6.5 | 0 | 3.8 | 1.3 | 0.147 |
| 7 | 6.5 | 3.3 | 3.6 | 0 | 0.141 |
| 7 | 6.5 | 3.3 | 3.9 | 1.3 | 0.137 |
| 4 | 6.5 | 3.3 | 3.6 | 0 | 0.142 |
| 4 | 6.5 | 3.3 | 3.7 | 1.3 | 0.143 |

What is claimed is:

1. A process for disrupting cells to produce a substantially cell-free polysaccharide which comprises contacting an aqueous cell-containing broth, obtained by the fermentation of a nutrient medium with a polysaccharide-producing slime forming species of Pseudomonas microorganism resistant to disruption by enzymes, with a sufficient amount of anionic surfactant to render said microorganism susceptible to enzymatic disruption followed by contacting said surfactant treated broth with sufficient protease enzyme to degrade the bacterial cells therein and recovering a substantially cell-free polysaccharide.

2. A process according to claim 1, wherein the microorganism is Pseudomonas NCIB 11592.

3. A process according to claim 1, wherein the surfactant is an alkali metal alkyl sulphate, alkylbenzene sulphonate, sulphated alkanol ethoxylate or sulphated alkanol, in which the alkyl chain contains at least 8 carbon atoms.

4. A process according to claim 1, wherein the medium is contacted with the surfactant at a pH below 6.0.

5. A process according to claim 1, wherein the enzyme is an alkaline protease.

6. A process according to claim 1 wherein the substantially cell-free polysaccharide is recovered by filtering to remove any residual solid matter.

7. A process according to claim 6, wherein the substantially cell-free solution is concentrated by ultrafiltration.

8. A process according to claim 6 wherein the microorganism is Pseudomonas NCIB 11592.

* * * * *